United States Patent [19]

Giebel et al.

[11] Patent Number: 4,767,924
[45] Date of Patent: Aug. 30, 1988

[54] APPARATUS FOR OPTICAL MONITORING WITH A HIGH PRESSURE LAMP CONNECTED TO A FIBER OPTIC CABLE

[75] Inventors: Hayo Giebel, Traubing; Viktor Baumgartner, Taufkirchen; Ralf-Dietrich Tilgner; Hans Heinold, both of Munich; Manfred Kühne, Furtwangen; Hartmut Federle, Ahrensburg; Rüdiger Arnold, Pegnitz; Werner Rech, Heinersreuth, all of Fed. Rep. of Germany

[73] Assignee: B.A.T. Cigarettenfabriken GmbH, Hamburg, Fed. Rep. of Germany

[21] Appl. No.: 87,565

[22] Filed: Aug. 19, 1987

[30] Foreign Application Priority Data

Aug. 19, 1986 [DE] Fed. Rep. of Germany ....... 3628088

[51] Int. Cl.[4] .............................................. G01N 9/04
[52] U.S. Cl. .................................. 250/223 R; 356/73; 250/227
[58] Field of Search ............... 250/223 R, 227, 571, 250/572; 356/73; 362/32, 120, 183, 194, 212; 313/570, 571; 209/536, 558, 582, 586, 655

[56] References Cited

U.S. PATENT DOCUMENTS

| 3,890,509 | 6/1975 | Maxey | 250/223 R |
|---|---|---|---|
| 3,953,730 | 4/1976 | Henry et al. | 250/227 |
| 4,562,735 | 1/1986 | Krippner et al. | 250/223 R |
| 4,639,592 | 1/1987 | Heitmann | 250/223 R |
| 4,644,176 | 2/1987 | Heitmann et al. | 250/572 |
| 4,645,921 | 2/1987 | Heitmann et al. | 209/536 |

FOREIGN PATENT DOCUMENTS 2017899 10/1979 United Kingdom .

Primary Examiner—David C. Nelms
Assistant Examiner—William L. Oen
Attorney, Agent, or Firm—Armstrong, Nikaido, Marmelstein & Kubovcik

[57] ABSTRACT

An apparatus for optical monitoring of the surface of rod-shaped smoking articles and/or filter rods for the tobacco industry comprises a conveying means transporting the rods perpendicularly to their longitudinal direction and a high-pressure lamp which serves as light source and which is connected via an optical fibre cable to a sensor block; the optical fibre cable is divided amongst at least two cross-section transformers with strip-shaped light exit regions whose light rays are directed via a further optical system from above and below respectively onto the line-shaped region of the surface of the rod. In addition the sensor block contains a row of photoelectric transducers which simultaneously the line-shaped surface region in the longitudinal direction of the rod and thereby pick up the light reflected at the surface of the rod.

An arrangement controlled by the production cycle clock pulse determines by comparison surface faults from the output signals of the photoelectric transducers dependent on the reflectivity of the line-shaped region of the surface.

16 Claims, 8 Drawing Sheets

APPARATUS FOR OPTICAL MONITORING WITH A HIGH PRESSURE LAMP CONNECTED TO A FIBER OPTIC CABLE

BACKGROUND OF THE INVENTION

1. Field of the Invention

The invention relates to an apparatus for optical checking or monitoring of the surface of rod-shaped smoking articles and/or filter rods for the tobacco industry comprising a conveying means transporting the rods perpendicularly to their longitudinal direction, a light source for irradiating the surface of a rod disposed in the test location, a row of photoelectric transducers which simultaneously scan a line-shaped surface region in the longitudinal direction of the rod and an arrangement controlled by the production cycle for the detection, made by comparison, of surface faults from the output signals of the photoelectric transducer dependent on the reflection capacity of the line-shaped region of the surface.

2. Description of the Prior Art

Below the problems occurring in the optical checking or monitoring of rod-shaped smoking articles and/or filter tips or rods will be explained with reference to the monitoring of cigarettes. However, similar problems also arise with cigars, cigarillos or filter rods or tips.

In the production of cigarettes very close tolerances must be kept to for various dimensions, in particular the diameter and the length, in order to ensure the desired product quality as constant and defined as possible.

Various constructional forms of optical inspection means which can be used in the tobacco industry are known from German Offenlegunsschrift No. 2,542,082, German Auslegungsschrift No. 2,332,813, German Auslegungsschrift 2,451,199, U.S. Pat. No. 4,093,866, U.S. Pat. No. 4,149,089 and U.S. Pat. No. 3,812,349.

Whereas with these inspection apparatuses only a random monitoring of individual smoking articles is possible with apparatuses of the type of the present invention for optical monitoring of the surface of rod-shaped smoking articles and/or filter rods for the tobacco industry, as described in German patent No. 3,030,140, even with the present-day high production speeds of the order of magnitude of about 6000 rods per minute all the surface faults can be detected, i.e. not only fluctuations in the dimensions but also holes or dirt spots on the surface of the cigarette paper, changes in the contour, folds, and fluctuations in the location or exact formation of an imprint or stamp.

For this purpose the known apparatus comprises a conveying means, generally a transport drum, transporting the rods perpendicularly to their longitudinal direction and located at a suitable point in the cigarette manufacturing plant, a light source for irradiating the surface of a rod located in the test location, a row of photoelectric transducers which simultaneously scan a line-shaped surface region in the longitudinal direction of the rod, a memory unit for the image points of a plurality of adjacent scanning lines and two-dimensional integrators for the two-dimensional signal processing which also takes account of the manufacturing duty cycle.

A similar apparatus is known from German Offenlegungsschrift No. 3,420,470 in which on a first conveying means a first test zone portion is provided and on a second conveying means a second test zone portion. On each test zone portion at least two optical test means are aligned at different angles to the conveying plane and illuminate and scan adjacent axis-parallel peripheral portions of the rods running through the particular test zone portion. Each optical test means consists of a light source illuminating the axis-parallel peripheral portion of the rods and an optoelectronic sensor having at least one row of optoelectrical detectors for detecting the light reflected at the article surface. The peripheral regions of the rods concealed on passage through the test zone portion face the optical test means on passage through the second test zone portion so that in contrast to the apparatus according to German patent No. 3,030,140 the entire surface of a rod can be scanned.

However, detailed investigations with such an inspection apparatus have shown that there is still room for improvement. In particular, the accuracy is not satisfactory in detecting surface errors at the aforementioned high production speeds which meanwhile may be up to 8000 rods per minute.

SUMMARY OF THE INVENTION

The invention therefore has as its object to provide an apparatus for optical inspection or monitoring of the surface of rod-shaped smoking articles and/or filter rods for the tobacco industry of the category specified in which the aforementioned disadvantages do not occur.

In particular, an apparatus is to be proposed which even at extremely high processing speeds of about 8000 rods per minute and more detects with great accuracy all the surface faults occurring in practice.

The invention therefore proposes in an apparatus for optical checking or monitoring of the surface of rod-shaped smoking articles and/or filter rods for the tobacco industry comprising a conveying means transporting the rods perpendicularly to their longitudinal direction, a light source for irradiating the surface of a rod disposed in the test location, a row of photoelectric transducers which simultaneously scan a line-shaped surface region in the longitudinal direction of the rod and an arrangement controlled by the production cycle for the detection, made by comparison, of surface faults from the output signals of the photoelectric transducer dependent on the reflection capacity of the line-shaped region of the surface, the improvement wherein the light source comprising a single high-pressure lamp is connected via an optical fibre cable to a sensor block which contains a further optical system directing the light rays emerging from the optical fibre cable onto the line-shaped region of the surface of the rod as well as the row of photoelectric transducers; and the optical fibre cable is divided among at least two cross-section transformers with strip-shaped light exit regions, the light beams of which are directed from above and below respectively onto the line-shaped region of the surface of the rod.

Advantageous forms of embodiment are defined by the features of the subsidiary claims.

The advantages achieved with the invention are due to the matching of the individual components of the overall system, i.e. the illumination means, the row of photoelectric transducers also referred to as "camera" and the signal preprocessing and evaluation, to achieve optimum conditions so as to make the optical/electrical relationships such that even minor surface faults can be detected with great accuracy.

For this purpose firstly a single arc source is used, in particular a high pressure lamp with short arc, which has an almost point-shaped light emission region and thus from the light-production side itself guarantees high homogeneity. This white-light lamp is operated in perpendicular position so that compared with the hitherto usual constructions an extremely long life is obtained.

Another contribution to long life is a strong cooling with high air throughput through a "special air convection flue". For the actual light source is disposed in a two-chamber system, the inner primary cycle formed as flue being sealed, i.e. the air coming into contact directly with the whitelight lamp rises in the "flue" thus formed and is thereby circulated. This inner outwardly sealed primary cycle is surrounded by the secondary cycle which is connected to the environment so that via a fan a constant air exchange is effected and as a result the heat emitted by the highpressure lamp to the inner housing can be carried away outwardly.

This optical part of the light source is disposed in a cast housing so that a very stable and thus largely vibrationfree structure results.

The light emitted by the high-pressure lamp is reflected via a special concave mirror surrounding the high-pressure lamp onto a deflection mirror with IR filter to the exit; the special layer provided on the deflection mirror serves to cut out IR radiation and thus as heat sink.

A further IR heat filter is disposed upstream of the exit, viewed from the beam direction, so that the outwardly directed light practically no longer contains any IR radiation.

Thus, at the outlet provided in the cast housing a focused and thus concentrated beam appears without any IR component.

For safety reasons at the outlet a guard flap is provided which can be electromechanically actuated and pivoted into the beam path. This actuation can be either manual or automatic, for example on withdrawing the optical fibre cable still to be explained from the outlet of the housing of the light source.

Connected to the outlet opening of the housing of the light source is the already mentioned bundle of optical fibres which can have a length of about 2 m and is connected to the actual sensor block which contains a further optical part which directs the light emitted by the optical fibres onto the surface of the rod as well as a row of photoelectric transducers hereinafter referred to as "camera". This sensor block is constructed as unit and made up on a cast part which serves as optical bench and at the same time as part of the housing; this gives a compact structure which can be adjusted and adapted to the specific conditions. At the same time, thermal expansion, thermal dissipation, etc., are taken into account.

An optical precision bench ensures a high resistance to vibration of the optical part; in addition interchangeable objectives can be provided and the distance between camera and optical system can be varied as required, this being done with high precision.

The bundle of light waveguides or optical fibres connected to the actual light source is divided into four sub-bundles and subjected to a cross-sectional transformation so that on the one hand two substantially strip-shaped light exit regions are formed and on the other hand at the edge also two additional optical fibre bundles result which serve for corner illumination as will be explained below.

This gives a very homogeneous light distribution in the longitudinal direction of the rod in that the light leaving the two strip-shaped light exit regions of the two optical fibres is directed via a lens array, a cylindrical lens, a deflection mirror and a further cylindrical lens from above and below respectively onto a strip-shaped region of the surface of the rod. At the same time via deflection mirrors light from the two small optical waveguide bundles is incident on the end regions of the surface of the rod, giving a strong edge illumination which also contributes to homogeneous light distribution over the entire surface projection of the visible part of the rod.

The entire focal depth region of the camera is thus very uniformly illuminated so that in particular exact diameter measurements are possible.

The light focus point of the optical part should not lie on the surface of the rod since otherwise the structure of the optical fibre cross-sectional transformers, in particular defective glass fibres, and of the optical components are imaged. It has therefore been found to be expedient for the focus point of the illumination to lie somewhat behind the rod viewed from the beam direction.

The light reflected at the surface of the rod passes through a colour filter so that specific colours, for example the stamp imprint, can be cut out or emphasized when the surface of the rod is illuminated with multicolour light, i.e. white light.

Sub-ranges can also be filtered out by using correspondingly different filters. To achieve great flexibility here the colour filter should be interchangeable so that it can be adapted, for example, to specific cigarette brands.

The colour filter should be located as close as possible to the exposure plane, i.e. the surface of the rod, to enable sub-regions to be defined properly as well. To achieve the desired blurred filter transitions this colour filter must be provided in the vicinity of the optical part whilst the aforementioned basic filtering for the IR radiation takes place directly at the light source. The filtering out of the IR radiation is essential not only for thermal protection reasons but also because of the IR sensitivity of the camera.

The cylindrical lenses and the lens array or raster extending in the horizontal direction also contribute to the desired homogeneous light distribution for the illumination plane on the surface of the rod from the point of view of the camera. Each optical fibre cross-sectional transformer and the rear cylindrical lens seen in the beam direction can be adjusted for beam balancing whilst the front cylindrical lens, the lens array, the deflection mirror and the cylindrical lens at the light exit window are stationary.

The photoelectric transducer is formed by charge-coupled or CCD elements in a linescan camera, the video signals being read out linewise and controlled in accordance with the production duty cycle; this gives a constant illumination time, i.e. the reading out of the charges of the individual pixels from the linescan camera is in a fixed timer raster during which the remaining time up to the next line readout is variable, i.e. depends on the production speed. This makes possible a very exact diameter detection even when the conveying speed of the rods changes.

In a prototype of such an optical monitoring or inspection apparatus a total of 1024 CCD elements is provided so that the video signal can consist of a maximum of 1024 individual analog signals. These signals can either be processed altogether or in groups by combining pixels for example in four groups each of 256 individual pixel signals, giving a sort of "magnifying effect". For in this manner it is now possible to select specific regions of the surface and to process and scan them with high, i.e. maximum, resolution, as is necessary for example for inspecting the stamp imprint.

If such an extremely high accuracy is not necessary 1024 individual signals can be combined in groups, for example in pairs or in groups of four, and the further processing thereby carried out with correspondingly reduced accuracy.

The resolution in the transport direction is the same with all speeds because a rigid coupling is maintained between the line-cycle clock, i.e. 128 rows, and the production speed; as a result the image generated on the camera is always of constant brightness and constant size in the article transport direction.

The CCD camera has two video output channels, the image information being read image point by image point, i.e. pixel by pixel. The reading out of a line is done serially, the channel B reading out the signals of the odd pixels and channel A the signals of the even pixels offset in time. The further processing is also at least partially in two channels with a frequency each of 10 MHz so that a processing speed of $2 \times 10$ MHz results; consequently, compared with the hitherto usual constructional forms the processing speed can be considerably increased from the point of view of the camera.

It has been found expedient if in the longitudinal direction grazing light is incident on the surface of the rod because from possible shadows protrusions and thus surface faults can be detected. This can be done easily by appropriate design of the spatial layout of the deflecting mirrors.

BRIEF DESCRIPTION OF THE DRAWINGS

The invention will be described in detail hereinafter with the aid of examples of embodiment with reference to the accompanying schematic drawings, wherein.

DESCRIPTION OF THE PREFERRED EMBODIMENTS

Figure 1:
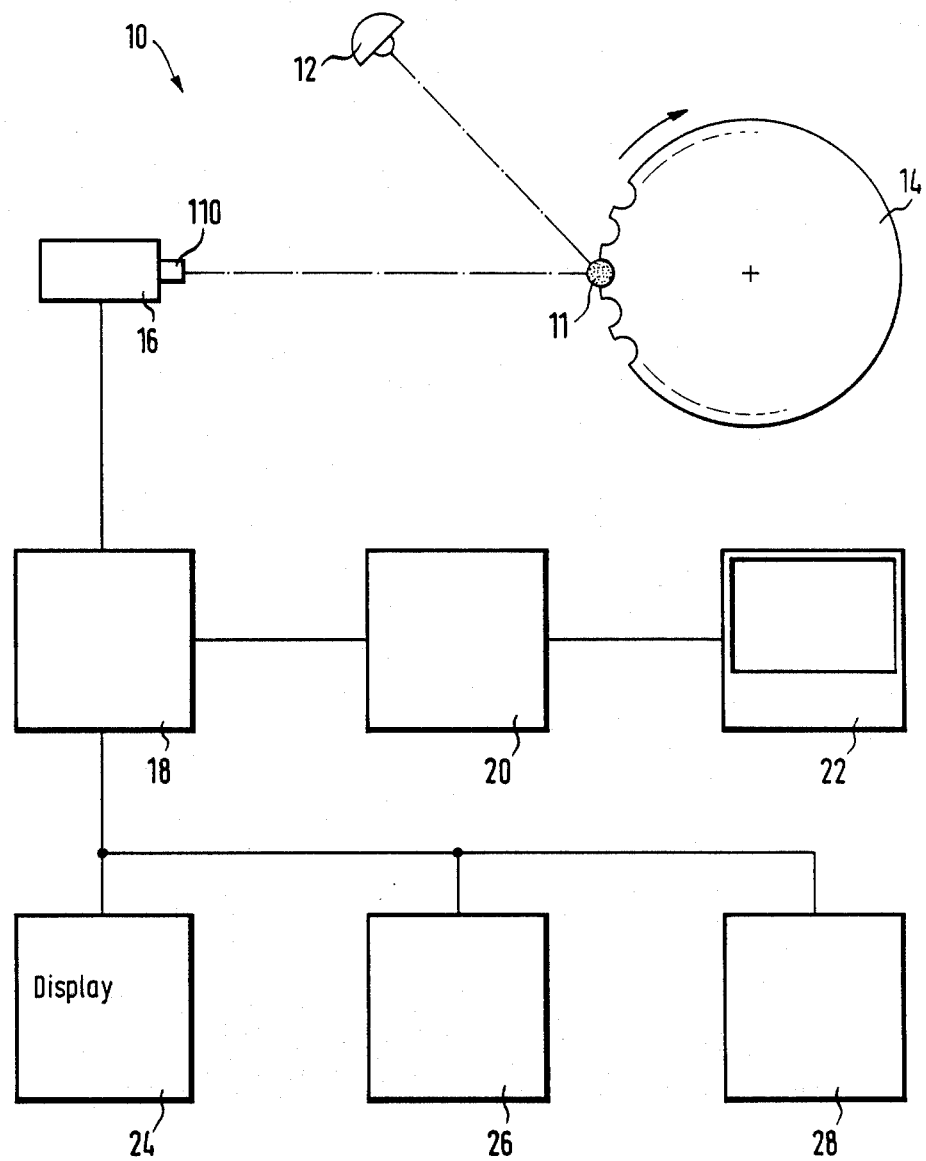
FIG. 1 is a basic illustration of the mechanical and optical parts of an apparatus for optical monitoring or inspection of cigarettes.

As apparent from FIG. 1 the apparatus 10 for optical inspection or monitoring of cigarettes comprises a so-called "linescan camera" which is indicated by the reference numeral 16 and includes a row of photosensitive elements arranged in a line, i.e. "charge-coupled elements" (CCD), a total of 1026 photosensitive elements guarantee an adequate resolution for the further processing.

In front of the row of photosensitive elements there is a schematically indicated objective lens 110 which permits focusing of the image on the photosensitive elements.

The cigarettes 11 to be monitored are supplied by means of a feed drum (not shown) to a transport drum 14 which is located at a suitable point in the cigarette manufacturing plant. For example as transport drum 14 a test drum for investigating the air impermeability of cigarettes may be used as is provided in some cigarette manufacturing machines.

The transport drum 14 needs only to fulfill the condition that the surfaces of the transported cigarettes 11 are at least partially exposed and can thus be subjected to the light from a light source 12 still to be explained. With the aforementioned test drum about 50% of the surface of each cigarette is exposed so that a proportion of the cigarette surface adequate for statistical evaluation can be scanned.

The cigarettes 11 are entrained by the drum in the direction of the arrow until they reach the point at which the surface of the drum 14 faces directly the objective of the linescan camera 16. At this point the drum surface is irradiated by a light source 12, the detailed construction of which is apparent from FIG. 3.

The light of the light source 12 reflected at the cigarettes 11 is incident through the objective 110 of the linescan camera 16 on the CCD elements so that it is converted to corresponding electrical signals whose amplitude depends on the intensity of the reflected light.

These analog video signals are subjected in processing electronics 18 to various transformations still to be explained so that in particular defective cigarettes 11 are detected and are ejected via an ejection means 28 provided on the cigarette making plant. Parallel thereto, images of specific selected cigarettes can be stored in an image memory 20 and displayed on a monitor 22.

Via a keyboard 24 combined with a display control data can be entered. A printer 26 serves as output unit and permits in particular the output of statistically relevant data.

Figure 2:
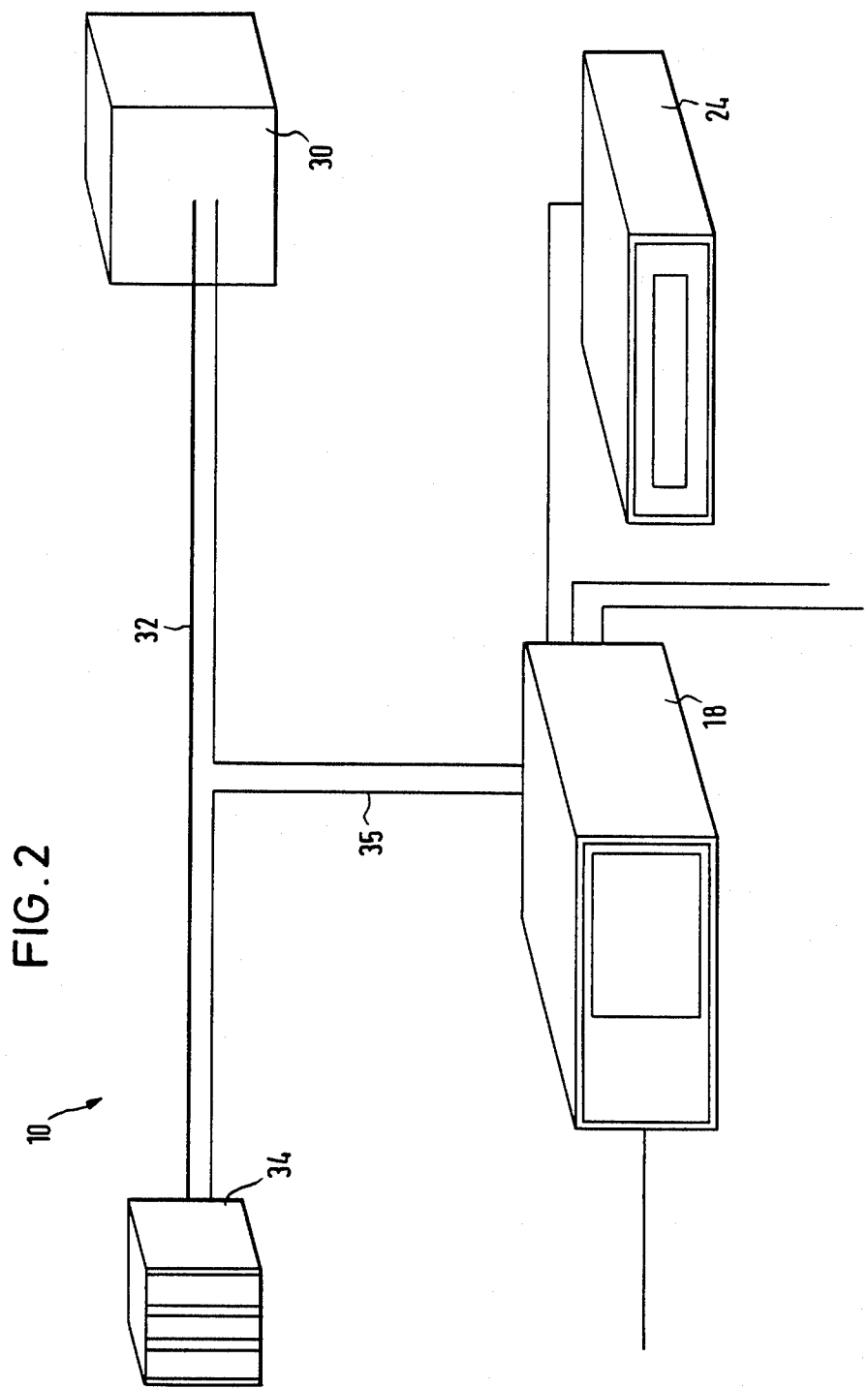
FIG. 2 shows in the form of a block circuit diagram a view of the overall structure of this apparatus.

FIG. 2 shows the overall configuration, i.e. a light source 30 which is connected via an optical fibre cable 32 which can be up to two meters long to a sensor block 34 which contains the linescan camera 16 and a further optical system still to be explained. This sensor block 34 is connected via a cable seven to ten meters in length to a computer 18 which is connected via a further cable seven to ten meters in length to the light source 30. The mains supply lead of the computer 18 is also shown in FIG. 2.

The computer 18 is also connected to a master computer for the overall cigarette production plant, to the cigarette making machine (not shown) and via a seven to ten meter long cable to the display 24 which displays specific selectable data, this being the rod length of a cigarette in the example illustrated in FIG. 2.

This "decentralization" of the apparatus 10 for monitoring the surface of cigarettes, i.e. the dividing of the apparatus into several components which are connected together via electrical or optical cables, permits flexible setting up of the individual components at suitable locations of the cigarette manufacturing plant.

Figure 3:
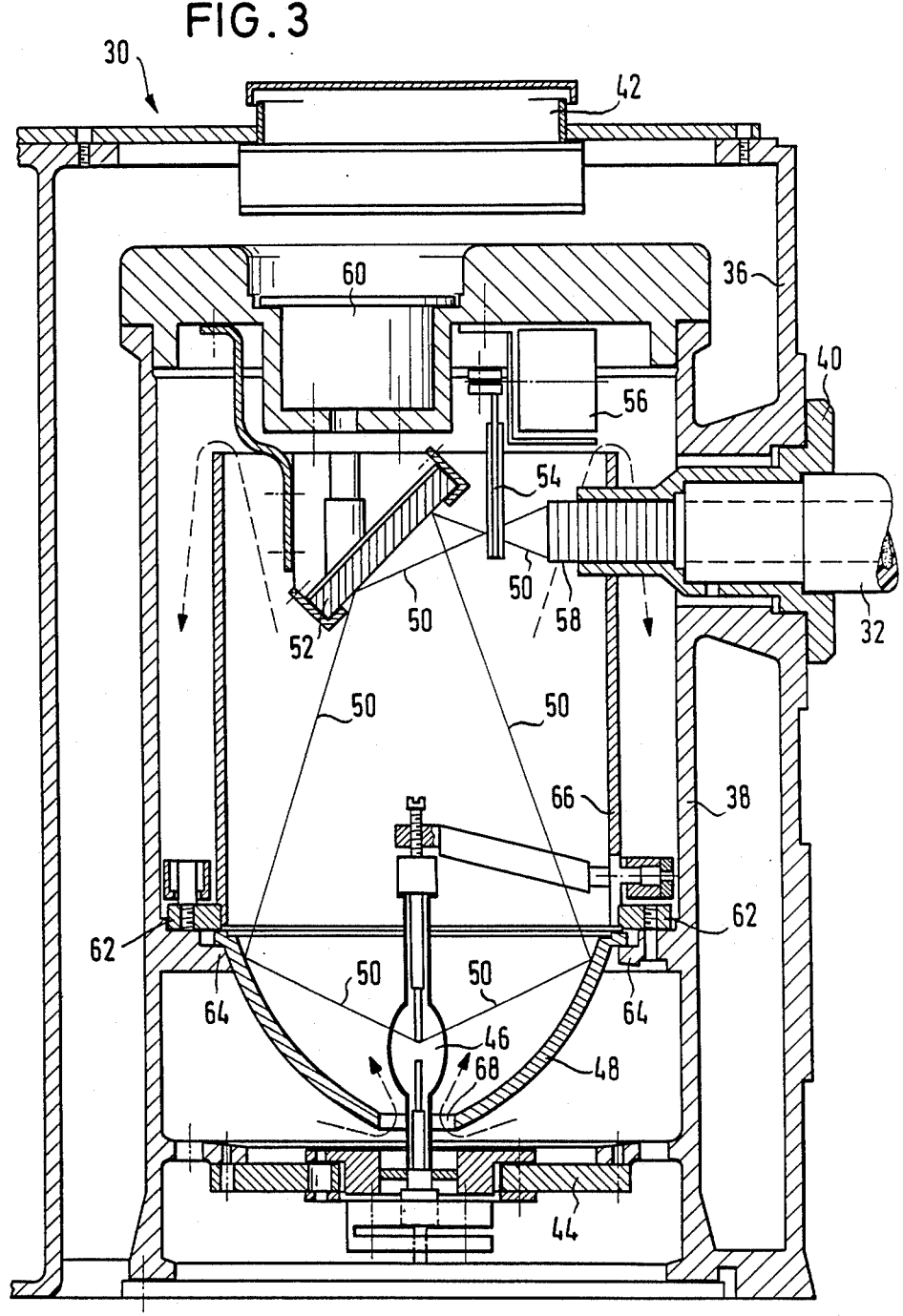
FIG. 3 is a vertical section through the light source.

The light source 30 shown in FIG. 3 has a housing 36 which is made as casting and which is formed integrally with a sealed inner housing 38. The housing 36 and inner housing 38 contain a through opening into which a socket 40 for connection of the optical fibre cable 32 is inserted.

At the upper side of the housing 36 there is a fan 42 for circulating or exchanging the air in the gap between the inner housing 38 and the housing 36.

In the outwardly sealed inner housing 38 in the region of the bottom thereof a holder 44 is provided for a short-arc high-pressure lamp or xenon lamp which is disposed in the vertical direction in an ellipsoidal mirror 48 in such a manner that the light generating point of the xenon highpressure lamp 46 is located in a focal point of the ellipsoidal mirror 48. As apparent in FIG. 3 a lamp holder 44 is disposed both above and below the xenon high-pressure lamp 46.

The ray path of the light emitted by the xenon high-pressure lamp 46 is indicated in FIG. 3 by the lines 50. It can be seen that the light emitted by the lamp 46 is reflected at the ellipsoidal mirror 48 upwardly to a deflection mirror 52 with IR bandpass filter and from the latter to the optical fibre cable 32. At the second focal point of the ellipsoidal mirror 48, which is located in the beam path illustrated behind the deflection mirror 52, a pivotable beam interruption plate 54 with an associated drive motor 56 is provided. By either manual or automatic activation the beam interruption plate 54 can be moved into the beam path to prevent light emergence from the inner housing 38 and thereby exclude any danger due to the highly concentrated light.

Disposed in the beam path between the deflection mirror 52 and the optical waveguide 32 there is a further IR filter 58 so that the light rays leaving the housing 36, 38 practically do not contain any IR radiation.

The planar deflection mirror 32 can be moved upwardly or downwardly by means of a drive means 60 as may be necessary for aligning the beam path with respect to the optical fibre cable 32.

As apparent in FIG. 3 the holder 62 for the ellipsoidal mirror 48 is secured on an encircling ring 64 at the inner face of the inner housing 38.

Whereas the air in the intermediate space between the inner housing 38 and the housing 36 is continuously replaced by ambient air by means of the fan 42 and thus circulated, the heat generated thereby being dissipated, the inner housing 38 is sealed as mentioned with respect to the outside; in said inner housing 38 there is a perpendicular hollow cylinder 66 adjoining the ellipsoidal mirror 48 at the top so that a sort of "flue effect" results; the air heated in the inner housing 38 by the heat generated by the xenon highpressure lamp 46 rises in the interior of the cylinder 36 and then flows in the gap between the wall of the inner housing 38 and the cylinder 66 downwardly until finally it flows through an opening 68 at the lower end of the ellipsoidal mirror 48 back into the ellipsoidal mirror 48 and there past the xenon high-pressure lamp 46 to cool the latter. The primary air flow path in the inner housing 38 resulting from this flue effect is indicated by the dashed arrows.

This light source 30 can be set up as independent constructional unit at a suitable point and connected via the optical waveguide cable 32 to the sensor block 34 which must be arranged with respect to the drum 14 in such a manner that the light emitted by the sensor block 34 and reflected at the surface of the cigarette 11 is incident on the linescan camera 16.

Figure 4:
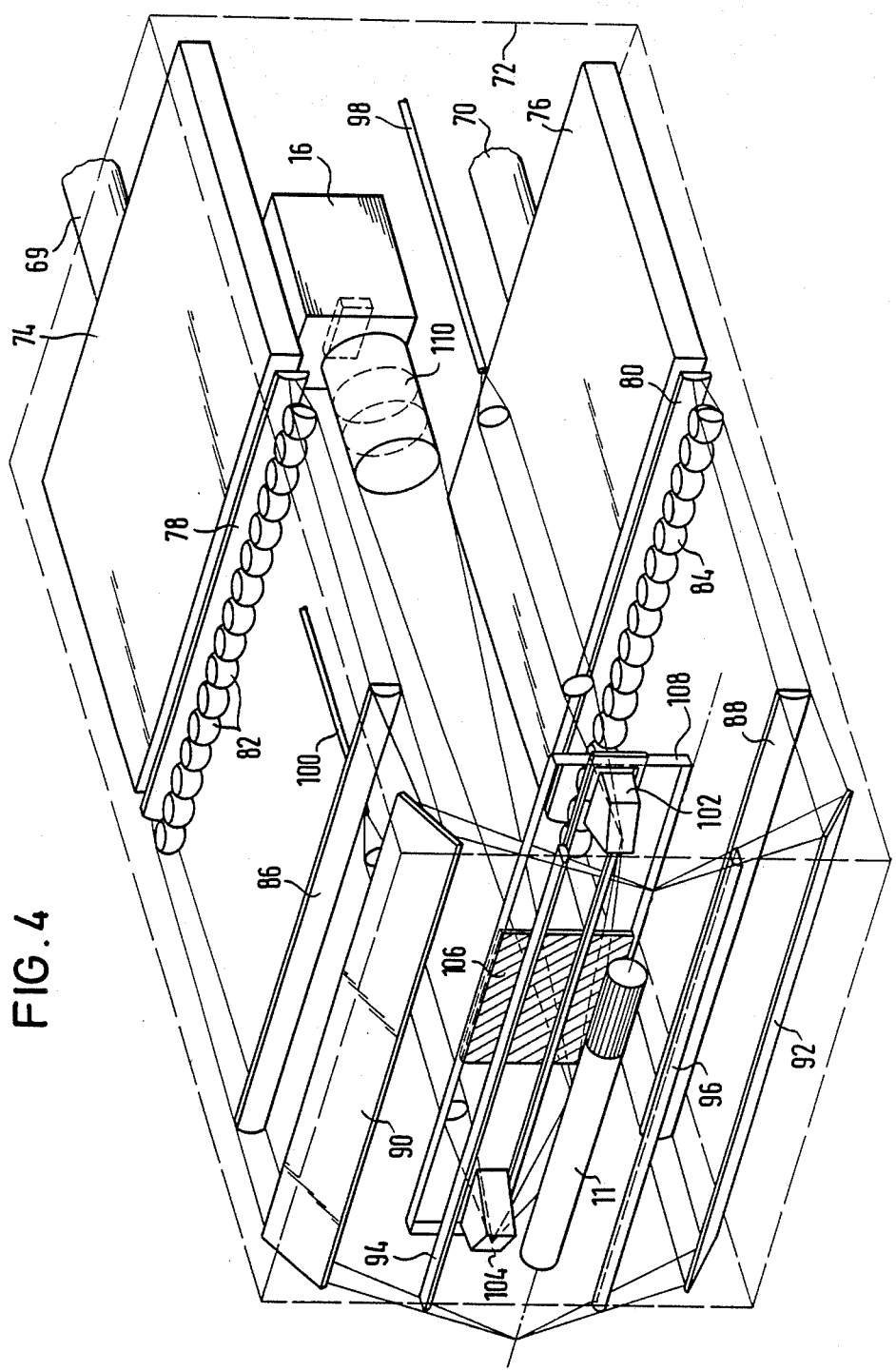
FIG. 4 is a perspective view of the sensor block with the CCD camera.

The structure of the sensor block 34 which is also formed as independent unit can be seen from FIG. 4. The optical fibre cable 32 consists of a great number of fine glass fibres which are divided into the two optical waveguides 69 and 70 shown in FIG. 4 which are introduced at the top and bottom into the housing 72 of the sensor block 34. Each optical waveguide 69, 70 opens into a cross-section transformer 74, 76, i.e. the incoming glass fibres of the optical waveguides 69, 70 are subjected to a cross-sectional transformation such that a strip-shaped light exit opening results which extends substantially over the width of the housing 72 of the sensor block 34.

In the beam path of the light emitted by the strip-shaped light exit regions of the two cross-section transformers 74, 76 there is in each case in series a cylindrical lens 78, 80, a lens array or raster lens 82, 84, a further cylindrical lens 86, 88, a deflection mirror 90, 92 which directs the strip-shaped beam downwardly or upwardly respectively, and a further cylindrical lens 94, 96 which concentrates the strip-shaped beam from above or below onto a strip-shaped region of the surface of the cigarette 11.

In addition, in FIG. 4 in the vertical centre between the two cross-section transformers 76, 74, i.e. substantially at the vertical height of the cigarette 11, on both sides two further optical waveguides 98, 100 branched from the cable 32 are shown and the light beams thereof are directed via corresponding corner deflection mirrors 102, 104 from the side onto the cigarette 11 and thereby ensure uniform illumination in the edge regions of the cigarette 11 which are always critical for homogeneous illumination.

The housing 72 of the sensor block 34 made as casting serves as optical bench for the adjustment of individual components. The light reflected at the cigarette 11 passes via a colour filter 106 secured by means of a holder 108 interchangeably in the housing 72 to the objective 110 of the linescan camera 16. The colour filter 106 is replaceably secured in the housing 72 so that the filter effect can be matched to the particular type of cigarette.

Figure 5:
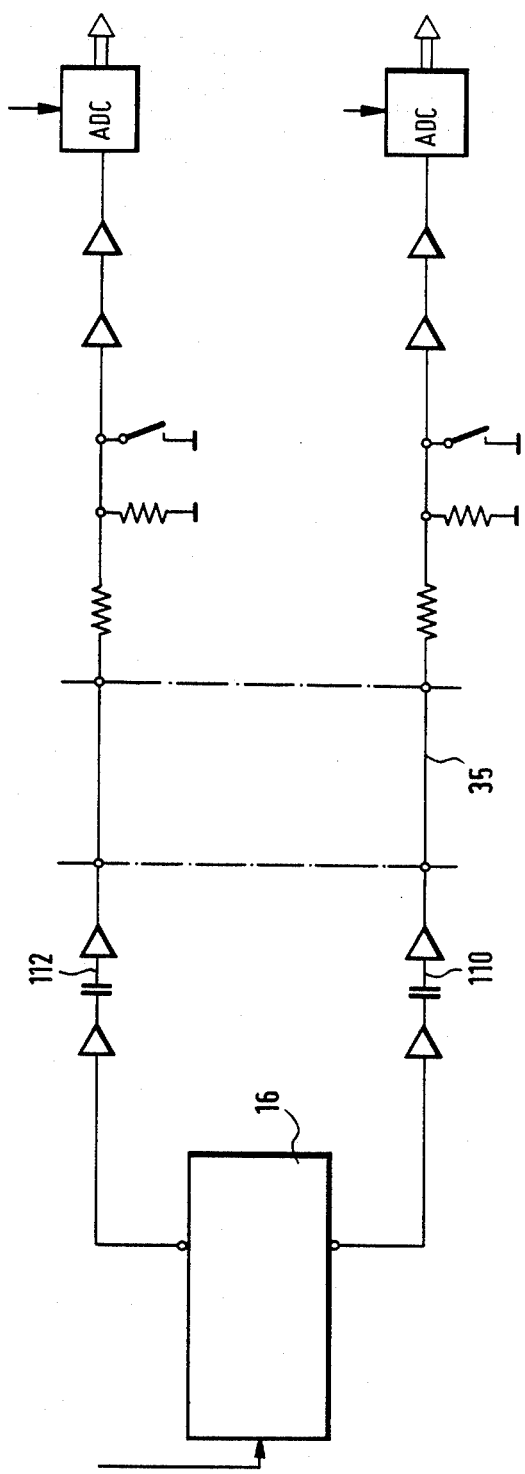
FIG. 5 is a block illustration of the CCD camera with the video signal flow.

As indicated in FIG. 5 the linescan camera 16 consists of a single chip having in this case for example 1024 CCD elements, the necessary preamplifier and the drive electronics. The CCD linescan camera has two video output channels A and B, the analog video signals being read out picture element by picture element. The reading out of the picture elements of a row is serially, the signals for the odd picture elements on channel B and the signals for the even picture elements on channel A being output offset in time. For controlling this operation the three camera drive signals shown in FIG. 5 are necessary, that is a shift clock signal, a tranfer clock signal and an illumination clock signal. These control signals ensure the correct functional sequence for generating the analog video signals on the two channels A and B.

The video signals on the two channels A and B are connected via impedance converters 110, 112 to the cable 35 which is connected to the computer 18.

In the computer 18 the analog video signals on the two channels A, B are supplied via output amplifiers and (coaxial) cable drivers indicated schematically in FIG. 5 to an analog/digital converter ADC which forms from the analog video signals corresponding digital video signals.

The two analog/digital converters ADC have means for zero value alignment and signal standardization as usual in this field .

Figure 6:
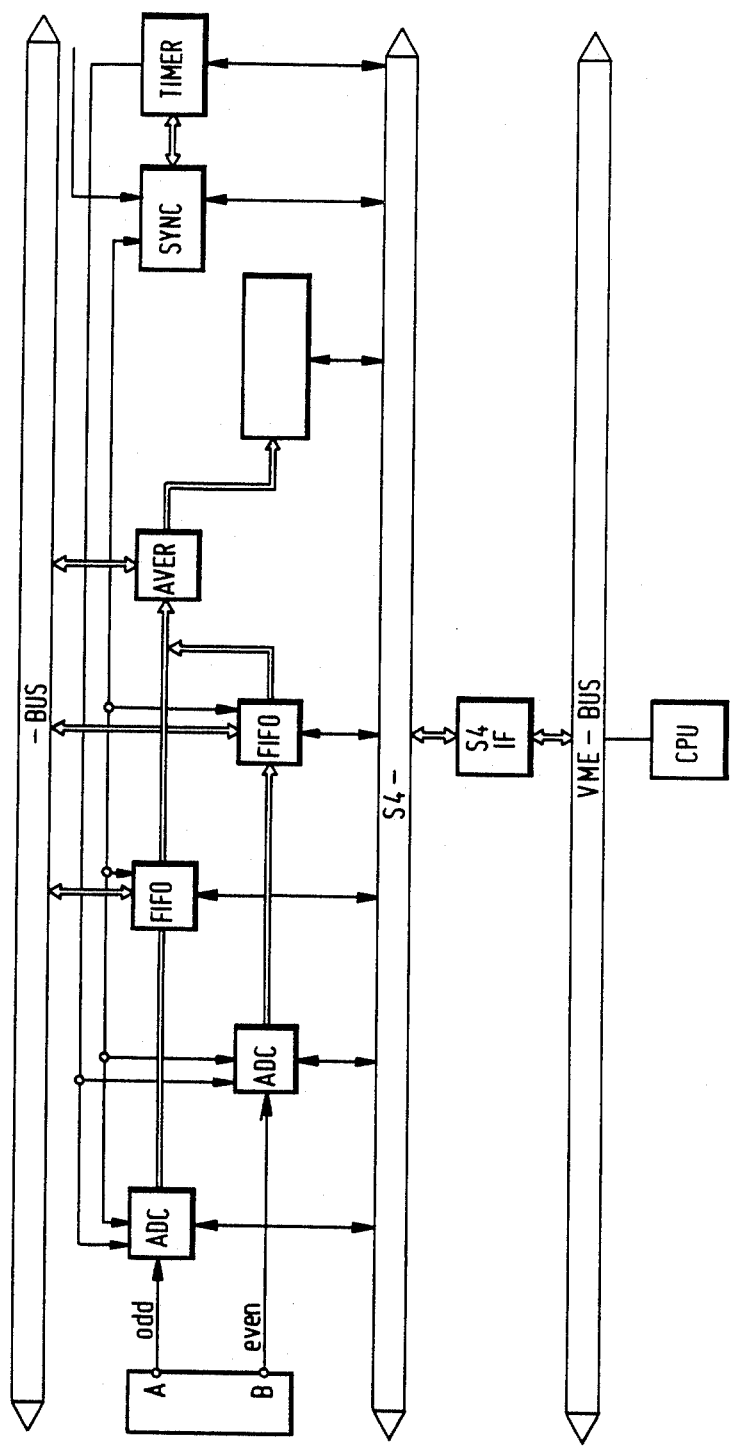
FIG. 6 is a basic illustration of the signal processing.

As apparent from FIG. 6 in which the basic principle of the signal processing is shown the analog/digital converters ADC are followed by buffers which operate by the "FIFO" principle and are designated by "FIFO". The digital video signals from the buffers "FIFO" are brought together in an averager AVER and then passed to the signal processing. The synchronization unit SYNC and a timer TIMER of the signal processing and the analog/digital converters ADC and the buffers FIFO are configured or controlled via an S4 control bus. The synchronization unit SYNC, which can be formed as sync board, performs the task of the control with respect to the outside, i.e. essentially for the linescan camera 16 and the machine interface, whilst the timer TIMER, which may be constructed as timer board, takes on the timing sequence and synchronization internally, i.e. essentially for the S4 control bus, the VME bus and the central processing unit CPU.

A further bus VIDEO BUS connected to the buffers FIFO and the averager AVER serves to derive the digital video signal from the preprocessing path and supply it to a service computer.

As already mentioned above, in the averager AVER the signal stream from the two channels A, B, that is from the two buffers FIFO, is combined and is made avaiable to the following signal preprocessing via the S4 control bus which is configured in a suitable manner. The S4 control bus is serviced from the S4 interface by the VME bus as apparent from FIG. 6.

Figure 7:
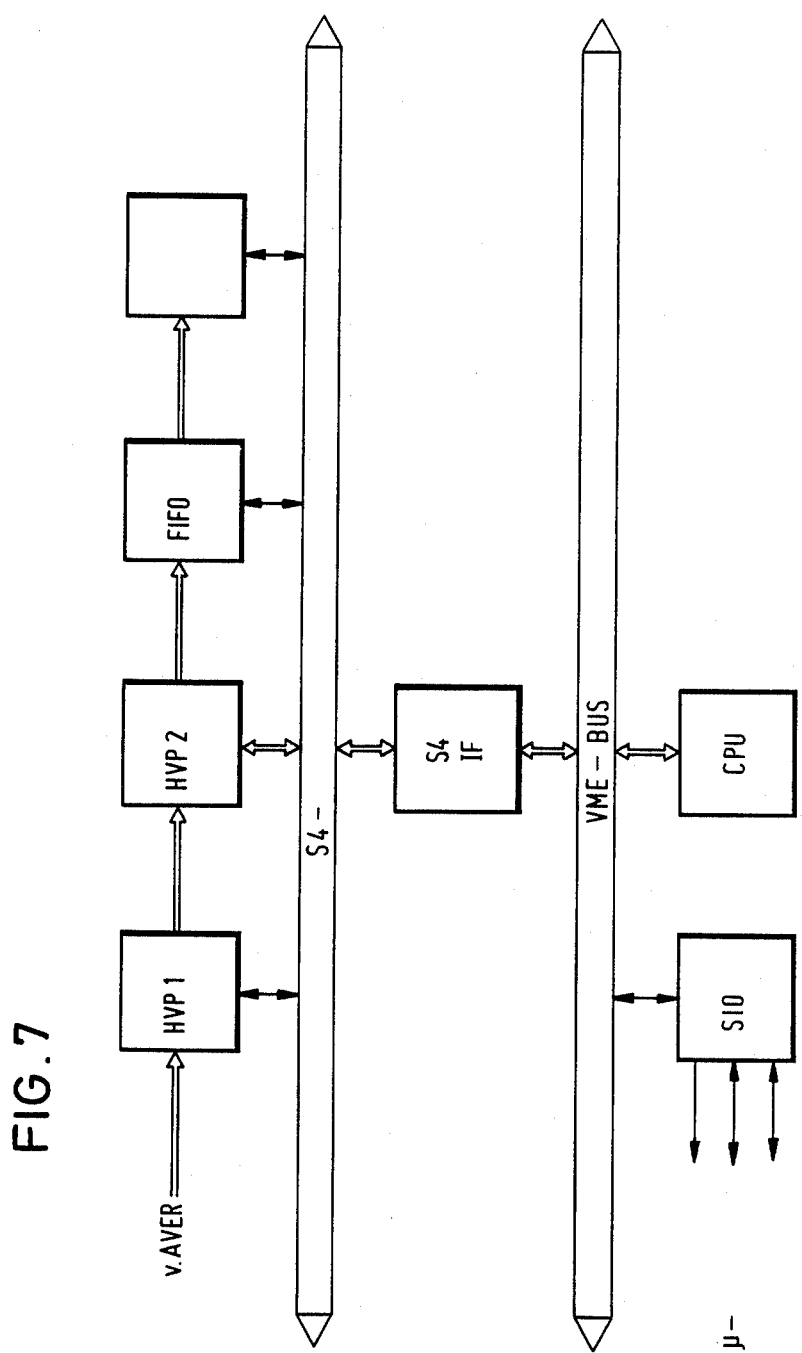
FIG. 7 is a basic illustration of the signal preprocessing and evaluation and FIG. 8 is a functional diagram of the computer referred to as "HVP II".

The further signal flow, i.e. the signal preprocessing and evaluation, is apparent in FIG. 7; the digital video signals from the averager AVER are supplied to the signal preprocessing which consists of a first computer HVP I, a second computer HVP II, a further buffer FIFO and a special processor which are each activatd via the S4 control bus.

The function of the first computer HVP I is described in German patent No. 3,030,140.

The signal evaluation is performed via the central processing unit CPU, a serial input/output interface card SIO and the machine interface which "combination" supply the essential results, that is
  statistics logs
  warning/alarm
  ejection
  stop machine The second computer HVP II performs the summation of lines in the horizontal and vertical direction, the formation of region, location and algorithm being generated in the computer HVP II from the special processor.

The serial input/output interface card SIO serves the "periphery", such as the display panel 24, the μ terminal, the master computer and the service communication.

The basic principle of the signal preprocessing and evaluation is already described in German patent No. 3,030,140 so that to avoid repetitions reference is made to the explanations therein, in particular as regards the two-dimensional signal processing with the aid of two-dimensional integrators.

The reading out of the analog video signals from the CCD elements of the linescan camera 16 is controlled by the production clock pulse thus giving a constant exposure time; the reading out of the charges of the individual picture elements from the individual CCD elements is in a fixed time raster, i.e. the reading out period of each picture element is constant, whilst the remaining time up to the next row readout is variable, that is depends on the particular production speed.

As a result, even when the production speed is changed the diameters of the individual cigarettes 11 can be detected with great accuracy.

Figure 8:
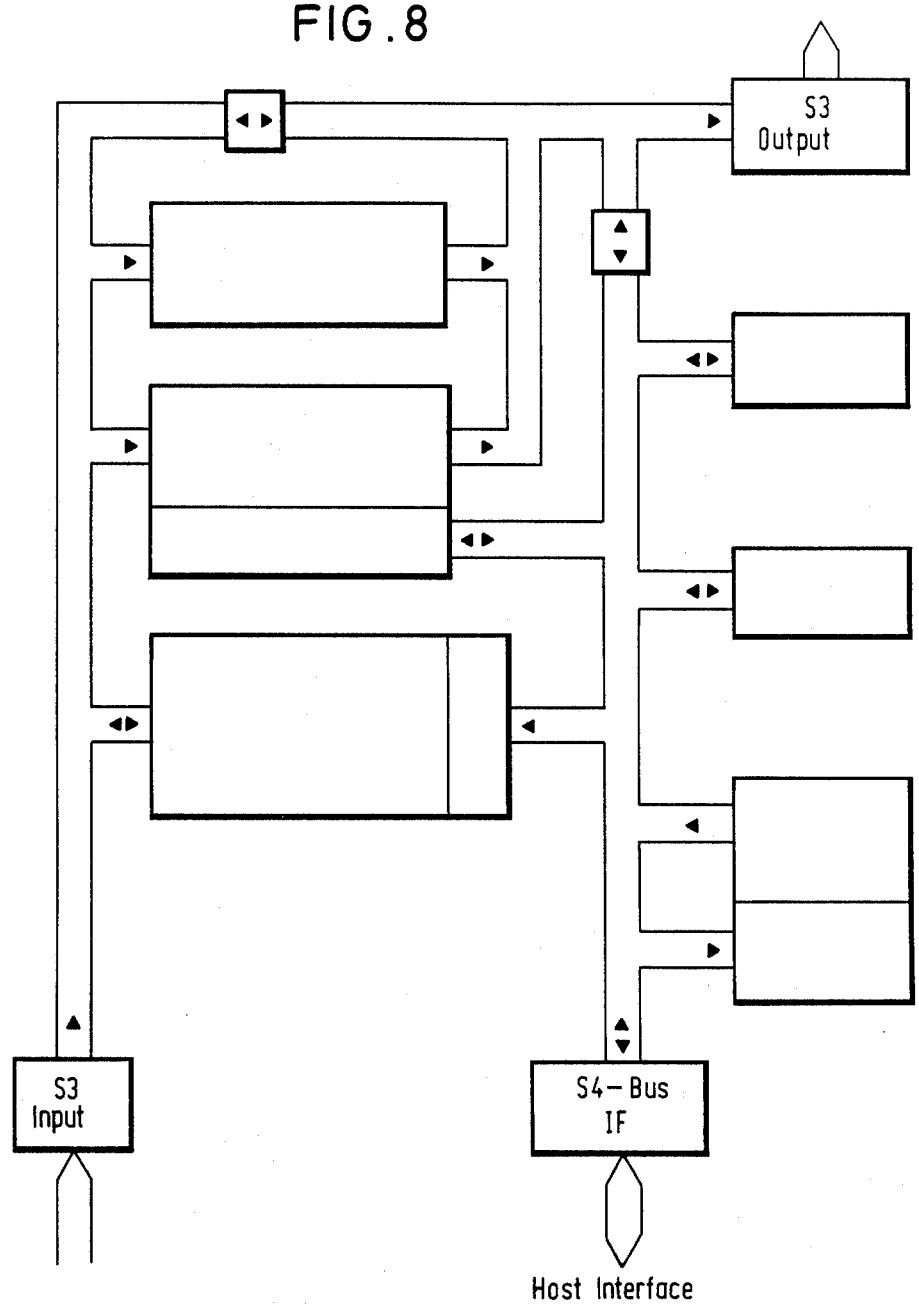

The second computer HVP II serves to evaluate the image in real time (FIG. 8). Byte-oriented data are processed at a data rate of 10 MHz, the nature of the processing/function being defined in a microprogram (MP) and the sequence of the functions dynamically controlled in the microprogram sequencer. As a result a cyclic image-synchronous operation is possible without host interaction.

The following functions are implemented and can be carried out simultaneously:
acquisition of an image from the data input "S3 input",
  entry of an image in the image memory, alternatively to the aformentioned acquisitions, output from the image memory for processing,
summation via elements of a row,
summation via elements of several columns when the elements are arranged in a row,
output of an image to the output "S3 output",
output of the column/row sums to the output "S3 output",
output of control codes of the microprogram MP to the output "S3 output".

Separately from the processing the parameterizing and the function test are carried out via the S4 bus interface. The parameterizing includes
  selection of a microprogram,
  the determination of the MP sequence mode,
  loading of the row check memories,
  selection of one of these row check memories,
  loading of the parameter memory.

The contents of the row check memories and the parameter memory define independent image parts on which the aforementioned processing functions are performed.

Thus, a set of a total of only four values, that is the start point in the X direction, the length in the X direction, the start point in the Y direction and the length in the Y direction, from the parameter memory defines one of several "windows", that is rectangular image fragments from the total representation. This window now acts on the image entry into the memory so that only a part of the offered image is transferred, or on the output so that only a part of the image memory is read out, or on the summations.

Superimposed on this control are the control signals of the row control memory which defines for each individual pixel whether it contributes to the sum, varying in accordance with the row and column summation.

The typical use of the computer HVP II is configured such that an image is written into the image memory and simultaneously evaluated, depending on the particular parameters. In the interval up to the start of the next image the output of the sums determined is carried out as well as the evaluation of further smaller windows.

In this manner a sort of "magnification" effect can be achieved in that not all the 1024 analog or digital video signals associated with the individual picture elements are processed but instead said digital video signals are combined to groups, for example four groups each of 256 digital video signals. Certain areas can be selected from these groups and displayed with increased resolution so that for example the filter or the stamp imprint can be very exactly checked.

The resolution in the transport direction is the same for all speeds because there is a rigid coupling between the row clock cycle, for example 128 rows, and the production speed, i.e. all the images and all the "windows" always have the same brightness and size.

We claim:

1. In an apparatus for optical checking or monitoring of the surface of rod-shaped smoking articles and/or filter rods for the tobacco industry
   (a) comprising a conveying means transporting the rods perpendicularly to their longitudinal direction,
   (b) a light source for irradiating the surface of a rod disposed in the test location,
   (c) a row of photoelectric transducers which simultaneously scan a line-shaped surface region in the longitudinal direction of the rod and
   (d) an arrangement controlled by the production cycle for the detection, made by comparison, of surface faults from the output signals of the photoelectric transducer dependent on the reflection capacity of the line-shaped region of the surface, the improvement
   wherein
   (e) the light source comprising a single high-pressure lamp is connected via an optical fibre cable to a sensor block which contains
      (e1) a further optical system directing the light rays emerging from the optical fibre cable onto the line-shaped region of the surface of the rod as well as
      (e2) the row of photoelectric transducers; and
   (f) the optical fibre cable is divided among at least two cross-section transformers with strip-shaped light exit regions, the light beams of which are directed from above and below respectively onto the line-shaped region of the surface of the rod.

2. Apparatus according to claim 1, wherein the high-pressure lamp is disposed in the first focal point of an ellipsoidal mirror which directs the emitted light via a deflecting mirror onto the inlet of the optical fibre cable.

3. Apparatus according to claim 2, wherein the deflecting mirror is formed as cold-light mirror with spectral bandpass characteristic for IR radiation.

4. Apparatus according to claim 2, wherein in the vicinity of the second focal point of the ellipsoidal mirror a beam interruption plate pivotable into the beam path is disposed.

5. Apparatus according to claim 2, wherein between the deflecting mirror and the optical fibre cable an IR filter is provided.

6. Apparatus according to claim 1, wherein the light source comprises an outer housing serving as optical bench and formed as integral casting and a sealed inner housing and wherein a fan is provided for exchanging the air between the environment and the outer housing.

7. Apparatus according to claim 6, wherein in the inner housing a hollow cylinder is provided which serves as "flue" and which adjoins the ellipsoidal mirror to form a primary gas cycle in the inner housing.

8. Apparatus according to claim 1, wherein the light beams emerging from the two cross-section transformers are each directed via a first cylindrical lens, a lens array, a second cylindrical lens, a deflecting mirror and via a third cylindrical lens onto the line-shaped region of the surface of the rod.

9. Apparatus according to claim 1, wherein into the sensor block at least two further optical fibre bundles of the optical fibre cable open, the light rays of said bundles being corner deflecting mirrors onto the lateral edge regions of the line-shaped surface of the rod.

10. Apparatus according to claim 1, wherein in the sensor block near the rod an interchangeable colour filter is disposed.

11. Apparatus according to claim 1, wherein the housing of the sensor block is formed as optical bench for the adjustment of the optical components.

12. Apparatus according to claim 1, wherein the analog output signals of the photoelectric transducers are read out serially separated into even and odd picture elements on two channels, subjected to an analog/digital conversion, buffered and then combined to form an average value.

13. Apparatus according to claim 1, wherein the analog video signals are read out line-by-line from the photoelectric transducers under the control of the production cycle clock pulse.

14. Apparatus according to claim 1, wherein the photoelectric transducers are charge-coupled elements (CCD) of a linescan camera.

15. Apparatus according to claim 14, wherein the reading out of the charges of the individual picture elements from the individual CCD elements is carried out in a fixed time raster with constant exposure time whilst the remaining time depends on the respective production speed or production clock cycle pulse.

16. Apparatus according to claim 1, wherein the output signals of the photoelectric transducers can be processed in groups with the aid of buffer stages.

* * * * *